(12) United States Patent  (10) Patent No.: US 8,176,920 B2
Young  (45) Date of Patent: *May 15, 2012

(54) ARTIFICIAL AIRWAY APPARATUS

(75) Inventor: Peter J. Young, Norfolk (GB)

(73) Assignee: International Patents Inc., Victoria, Mahe (SC)

( * ) Notice: Subject to any disclaimer, the term of this patent is extended or adjusted under 35 U.S.C. 154(b) by 828 days.

This patent is subject to a terminal disclaimer.

(21) Appl. No.: 11/597,648

(22) PCT Filed: May 25, 2005

(86) PCT No.: PCT/EP2005/005754
§ 371 (c)(1),
(2), (4) Date: Jan. 4, 2008

(87) PCT Pub. No.: WO2005/118039
PCT Pub. Date: Dec. 15, 2005

(65) Prior Publication Data
US 2008/0283052 A1    Nov. 20, 2008

(30) Foreign Application Priority Data
May 27, 2004   (GB) .................................... 0411858.4

(51) Int. Cl.
*A61M 16/00* (2006.01)
(52) U.S. Cl. .......... 128/207.14; 128/200.24; 128/200.26

(58) Field of Classification Search ............. 128/200.24, 128/200.26, 205.19, 207.14, 207.15–207.17; 604/163, 118, 119, 171, 192, 263, 267, 256, 604/523, 533–539, 284, 93.01, 95.02, 264, 604/258, 94.01, 101, 101.01, 101.02, 101.05, 604/103.04, 103.05, 96.01, 107, 532, 912, 604/915, 919; 606/108, 159, 191–198
See application file for complete search history.

(56) References Cited

U.S. PATENT DOCUMENTS

| 4,305,392 | A |   | 12/1981 | Chester et al. |            |
|-----------|---|---|---------|-----------------|------------|
| 4,327,721 | A | * | 5/1982  | Goldin et al.   | 128/207.15 |
| 4,502,482 | A | * | 3/1985  | DeLuccia et al. | 128/207.15 |
| 4,762,125 | A | * | 8/1988  | Leiman et al.   | 128/207.15 |

(Continued)

FOREIGN PATENT DOCUMENTS

DE    19734821    2/1999

(Continued)

OTHER PUBLICATIONS

European Patent Office, International Search Report for PCT/EP2005/005754 mailed Sep. 22, 2005, 5 pages.

*Primary Examiner* — Annette Dixon
(74) *Attorney, Agent, or Firm* — Wilmer Cutler Pickering Hale and Dorr LLP (57) ABSTRACT

The invention relates to apparatus (19) for use in establishing an artificial airway in a patient, the apparatus comprising a tube (19a) for introduction into the patient's trachea for passage of gases to and from the patient's lungs, an inflatable seal (20) disposed upon the tube (19a) to provide, on inflation, a seal between the tube and the trachea of the patient, the seal (20) thereby defining a lung-side portion (19c) of the apparatus and a mouth-side portion (19d) of the apparatus, the apparatus further having the ability to facilitate removal of fluid from at or adjacent the said mouth-side portion (19d) of the apparatus (19).

14 Claims, 5 Drawing Sheets

U.S. PATENT DOCUMENTS

| | | | | |
|---|---|---|---|---|
| 4,840,173 | A * | 6/1989 | Porter, III | 128/207.15 |
| 5,143,062 | A * | 9/1992 | Peckham | 128/207.14 |
| 5,146,916 | A * | 9/1992 | Catalani | 128/207.14 |
| 5,311,864 | A * | 5/1994 | Huerta | 128/207.15 |
| 5,372,131 | A * | 12/1994 | Heinen, Jr. | 128/207.15 |
| 5,499,625 | A * | 3/1996 | Frass et al. | 128/207.15 |
| 5,501,215 | A | 3/1996 | Huerta et al. | |
| 6,062,223 | A * | 5/2000 | Palazzo et al. | 128/207.15 |
| 6,460,540 | B1 * | 10/2002 | Klepper | 128/207.14 |
| 6,941,950 | B2 * | 9/2005 | Wilson et al. | 128/207.14 |
| 7,089,942 | B1 * | 8/2006 | Grey | 128/207.14 |
| 7,121,280 | B2 * | 10/2006 | Kyle, Jr. | 128/207.14 |
| 7,293,561 | B2 * | 11/2007 | Madsen et al. | 128/207.14 |
| 7,360,540 | B2 * | 4/2008 | Brain et al. | 128/207.14 |
| 7,452,345 | B2 * | 11/2008 | Darouiche et al. | 604/22 |
| 2004/0079376 | A1 | 4/2004 | Melker | |

FOREIGN PATENT DOCUMENTS

| | | |
|---|---|---|
| GB | 2324735 | 11/1998 |
| WO | WO-99/38548 | 8/1999 |
| WO | WO-03/061747 | 7/2003 |

* cited by examiner

ARTIFICIAL AIRWAY APPARATUS

CROSS-REFERENCE TO RELATED APPLICATIONS

This application is a national stage application under 35 U.S.C. §371 of International Patent Appln. PCT/EP2005/005754, designating the United States and filed on May 25, 2005, which is incorporated herein by reference.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

INCORPORATION-BY-REFERENCE OF MATERIAL SUBMITTED ON A COMPACT DISC

Not Applicable.

BACKGROUND OF THE INVENTION

1. Field of the Invention

The present invention relates to artificial airway apparatus for use in establishing an artificial airway in a patient, and in particular to an artificial airway device which includes a balloon or similar device for sealing the trachea against unwanted escape of gases when the device is in place.

2. Description of Related Art Including Information Disclosed Under 37 C.F.R. 1.97 and 1.98

Artificial airway devices are well known in the art as described for example in GB 2324735 and WO 03/061747. Such devices include means to seal the space around the inserted tube when it is in place in a patient's trachea in order to prevent the uncontrolled escape of gases intended for the patient's lungs. WO 03061747 describes an ETT (endotracheal tube) which includes a silicone tubular member and an inflatable silicone cuff, or balloon, which is attached to the tubular member near its distal end. Upon inflation, the silicone cuff reaches its pressure plateau before the cuff is large enough to make circumferential contact with the inner lining of the smallest normal human trachea with which the ETT will be used. Furthermore WO 03061747 incorporates a metal spiral into the silicone tube removing the problems associated with silicone tubes and allowing the cuff to be easily attached to the tubular member.

BRIEF SUMMARY OF THE INVENTION

Although the provision of a balloon or cuff, or some such expedient solves the problem of gas escape, it can itself cause problems. One such problem is caused by the high sealing efficiency that can be achieved by some balloons and cuffs in the trachea. When the device is properly in place in a patient, the tube extends into the trachea with the balloon or cuff forming a seal around the tube, between the tracheal wall and the tube. The balloon or cuff defines, in effect, upper and lower, or lung side and mouth side sections of the airway. If the balloon or cuff in the trachea is fully effective in preventing passage of fluid, in some cases liquids such as the patient's own secretions can accumulate and pool above, or on the mouth side of the balloon or cuff. The accumulation of such secretions is a problem because it can form a reservoir for the growth of microorganisms such as bacteria. The growth and proliferation of bacteria in the trachea is itself extremely undesirable, and more so if on removal of the tube they pass into the lungs, which can result in the development of pneumonia. It is an object of the invention to seek to mitigate problems such as this.

According to the invention there is provided apparatus for use in establishing an artificial airway in a patient, the apparatus comprising a tube for introduction into the patient's trachea for passage of gases to and from the patient's lungs, an inflatable seal disposed on the tube to provide, on inflation, a seal between the tube and the trachea of the patient, the seal thereby defining a lung-side portion of the apparatus and a mouth-side portion of the apparatus, the apparatus further comprising means to facilitate removal of fluid from at or adjacent the said mouth-side portion of the apparatus. Thus, it can be seen that apparatus according to the invention allows for removal of accumulated fluids on the mouth-side portion of the apparatus thereby preventing said fluids from passing into the lungs on removal of the apparatus.

It is preferred that the fluid removal means comprises a plurality of ports in a wall of the tube on the mouth-side portion of the apparatus each port opening into a conduit, the conduit being in fluid communication with an aperture located to be outside of the patient when the apparatus in use, the arrangement being such that suction applied to the aperture causes fluid to pass into each port, along the conduit and out of the aperture. This is a convenient arrangement which allows the removal of fluid by suction and furthermore guards against the possibility that removal of fluid may be prevented by blockage if a single port only is provided.

The ports may be circumferentially spaced around the tube. This has the advantage that it makes it more likely that at least one port will remain free and open for removal of fluid, whatever the orientation of the tube within the patient. It is envisaged that in some situations, the application of suction might cause blockage of a port if that port is in close proximity to the lining of the trachea. The ports may also be longitudinally spaced along the length of the tube on the mouth-side portion of the apparatus. Again, this will assist in preventing the apparatus from ceasing to function for removal of fluids, and will also assist in removing fluids from other areas in the airway above the seal, such as the larynx, pharynx and oral spaces. This enables emptying of anatomically separated pools of secretions throughout the upper airway.

For ease of construction and economy of space it is preferred that the conduit is formed integrally in the wall of the tube.

In a first alternative construction, the apparatus may include a single aperture located to be outside of the patient when the apparatus is in use, in fluid communication with every port via a single conduit. Providing only a single conduit in the wall of the tube makes for the possibility of a narrower and more anatomically acceptable tube.

Alternatively, there may be two apertures located to be outside of the patient when the apparatus is in use, a first aperture communication with a first group of ports via a first conduit, and a second aperture communicating with a second group of ports via a second conduit. This arrangement provides a fail-safe mechanism, in that if one port/conduit/aperture combination becomes blocked, there is a second. In addition, this arrangement will provide for an alternative operation of the device in which a washing fluid can be injected through one aperture/conduit/port combination and removed via the other to provide a flushing action to the area on the mouth-side of the apparatus.

It will be appreciated that the or each conduit will, in use, come into contact with biological material such as microorganisms. It is preferred therefore that the or each conduit includes on its inner surface, a material adapted to reduce friction, reduce adhesion of material, and reduce or inhibit microbiological growth. Such materials can be selected from parylene and hydrogel-derived materials, antibiotics and bacterio static substances.

The apparatus may further comprise valve means disposed to limit fluid flow direction in the or each conduit. Thus, for example, in apparatus comprising a single conduit, a unidirectional valve installed in the conduit will prevent undesirable back flow of fluid after suction applied to the aperture has ceased.

A further method of preventing port blockage by ingress of tissue is to provide blockage prevention means in the form of one or more protrusion or upstand, extending outwards, from the tube wall adjacent the or each port. A protrusion will have the effect of holding the port away from the tracheal mucosa to assist in preventing entry of the mucosa into the port upon application of suction.

In one preferred embodiment of the apparatus, the tube may define a first zone and a second zone, at least a portion of the first zone having a first outer diameter, the second zone having a second outer diameter, the first outer diameter being smaller than the second outer diameter, the first zone being adjacent to the second zone and the first and second zones being configured for insertion into the patient's trachea, the inflatable seal comprising a cuff attached to the tube such as to extend over at least a portion of the first zone. The cuff may preferably be characterised by having an unstretched diameter smaller than said first outer diameter.

The cuff and/or the tube may comprise silicone.

According to a second aspect of the invention, there is provided apparatus as defined above in the form of an endotracheal tube.

According to a third aspect of the invention, there is provided apparatus as defined above in the form of a tracheostomy tube.

According to a fourth aspect of the invention there is provide a method of providing an artificial airway in a patient, the method comprising the step of applying apparatus according to any proceeding claim to the patient.

The method may further include the step of applying suction to an aperture of the apparatus for removal of fluid from the mouth-side of the apparatus via the ports and conduit. In particular, where apparatus with dual conduits is employed the method may include the step of passing a fluid into the apparatus via a first aperture/conduit/port combination and removing the fluid and entrained matter via a second aperture/conduit/port combination.

BRIEF DESCRIPTION OF THE DRAWINGS

The invention will further be described by way of example only, with reference to the following drawings, in which.

DETAILED DESCRIPTION OF THE INVENTION

Figure 1A:
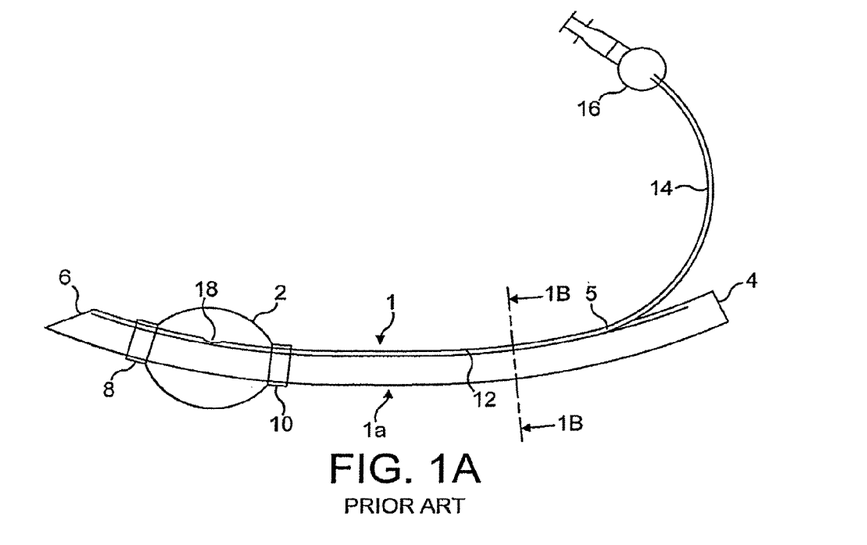
FIG. 1A is a schematic drawing of a prior art ETT (endotracheal tube)
Figure 1B:
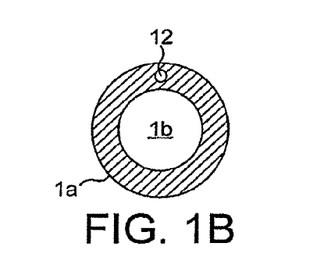
FIG. 1B shows a magnified sectional view of the ETT of FIG. 1 taken along the line 18-1B.

Referring to the drawings, FIG. 1A shows a prior art endotracheal tube (ETT) 1. FIG. 1B shows a magnified sectional view of ETT 1 taken along line 1B-1B as shown in FIG. 1A. ETT 1 includes a semi-rigid hollow tube 1a, which extends from a proximal end 4 to a distal end 6. Tube 1a is made from poly-vinyl-chloride (PVC). ETT 1 further includes an inflatable balloon, or cuff, 2 mounted near distal end 6. Balloon 2 is sealed to hollow tube 1a at locations 8 and 10 to form an airtight space within the balloon. ETT 1 further includes a central airway lumen 1b, which extends from the proximal end 4 to the distal end 6 of hollow tube 1a. Hollow tube 1a further defines a small inflation lumen 12, which extends through the wall of hollow tube 1a.

Inflation lumen 12 provides an opening 18 near its distal end within the interior volume of the balloon 2. At location 5, near the proximal end of hollow tube 1a, the inflation lumen 12 is connected to an inflation line, or tube, 14. An air syringe, automated pressure control device, or other suitable air supply, connected to the proximal end of inflation line 14 selectively controls inflation and deflation of balloon 2. FIG. 1A shows balloon 2 in an inflated condition.

In operation, the distal end 6 of ETT 1 is inserted into the mouth of an unconscious patient, through the patient's natural airway, until the distal end 6 extends into the patient's trachea. The proximal end 4 remains outside the patient. Balloon 2 is in a deflated condition while distal end 6 is being inserted into the patient. After distal end 6 has been positioned within the trachea, balloon 2 is inflated (e.g. by syringe 16) until the outer wall of balloon 2 forms a seal with the inner mucosal lining of the trachea. Once such a seal has been established, a ventilator coupled to the proximal end 4 of ETT 1 may be used to apply intermittent positive-pressure ventilation (IPPV) to the patient. During IPPV, medical gases supplied to the proximal end 4 of ETT 1 by the ventilator effectively forces the gases through airway lumen 1b and into the patient's lungs. However, if a seal is not established between balloon 2 and the interior lining of the trachea, gas forced out of distal end 6 simply escapes through the space between balloon 2 and the interior lining of the trachea, and out of the patient's mouth, instead of being forced into the patient's lungs.

Referring now to FIGS. 2 to 12 of the drawings there is illustrated apparatus 19 according to the invention for use in providing an artificial airway in a patient. The apparatus 19 is similar in construction to that which is illustrated in FIGS. 1A and 1B, sharing many features with that device. The apparatus 19 according to the invention comprises a tube 19a for introduction into the patient's trachea for passage of gases to and from the patient's lungs, an inflatable seal 20 disposed upon the tube 19a to provide, on inflation, a seal between the tube 19a and the trachea of the patient, the seal 20 thereby defining a lung-side portion 19c of the apparatus 19 and a mouth-side portion 19d of the apparatus 19, relative to the patient's anatomy when the apparatus 19 is in position. However, as distinct from the apparatus of FIGS. 1A and 1B, the apparatus 19 according to the invention further comprises means 19e to facilitate removal of fluid from at or adjacent the said mouth-side portion 19d of the apparatus 19.

Figure 2:
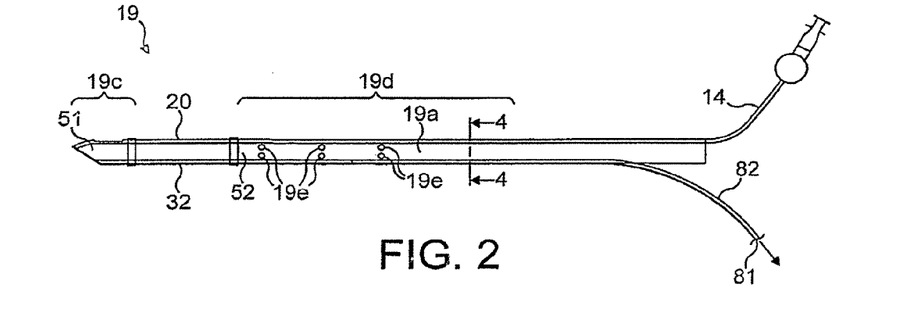
FIG. 2 shows an ETT constructed according to the invention.

In FIG. 2, the artificial airway device or apparatus 19 takes the form of an endotracheal tube (ETT). The ETT 19 includes a tube, or tubular member 19a, and a cuff, or balloon, 20 mounted near the distal end of tube 19a. Tube 19a and cuff 20 are both made of silicone. The Durometer (or hardness) of the silicone used to fabricate tube 19a may be about 80 Shore A. A suitable source of silicone for fabricating tube 19a is Dow Corning, Midland, Mich., or Wacker Silicone in Germany. Tube 19a may be between 5-100 cm in length for adult sizes.

Use of a silicone cuff 20 is advantageous because, silicone does not have the allergic effects associated with latex, and silicone has a longer shelf life than latex. Use of a silicone tube 19a facilitates attachment of cuff 20 to the tube 19a since methods of adhering silicone to silicone are well known in the art. Also, dimensions of the tube 19a and the cuff 20 are adjusted so as to advantageously provide an adequate air supply to the patient's lungs during IPPV via a main lumen 40 and so as to insure that the cuff 20 reaches its pressure plateau before making circumferential contact with the inner lining of the trachea. Accordingly, as described in detail in GB 2324735 and WO 03/061747, ETT 19 facilitates measurement of the mucosal pressure and further facilitates avoidance of excessive mucosal pressures. Also, use of the silicone cuff 20 provides improved seals with the trachea and avoids the wrinkles and microleaks associated with inelastic cuffs.

Figure 9:
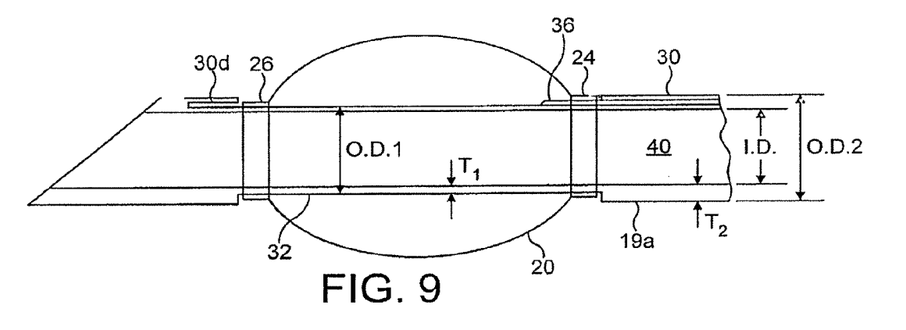
FIG. 9 is a magnified transverse sectional view showing a region of reduced diameter in an ETT constructed according to the invention.

In ETT 19, the cuff 20 is mounted to tube 19a in a region, or zone, 32 of reduced diameter (see FIG. 9). That is, in region 32, the outer diameter of tube 19a is reduced as compared with the outer diameter at other portions of tube 19a.

Figure 3:
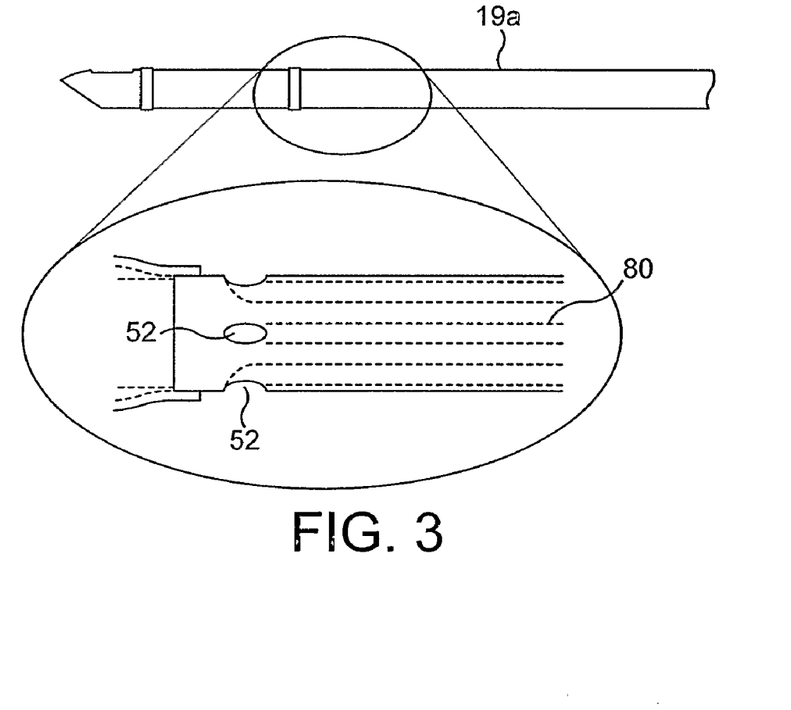
FIG. 3 is a magnified view of a part of the ETT of FIG. 2.
Figure 4:
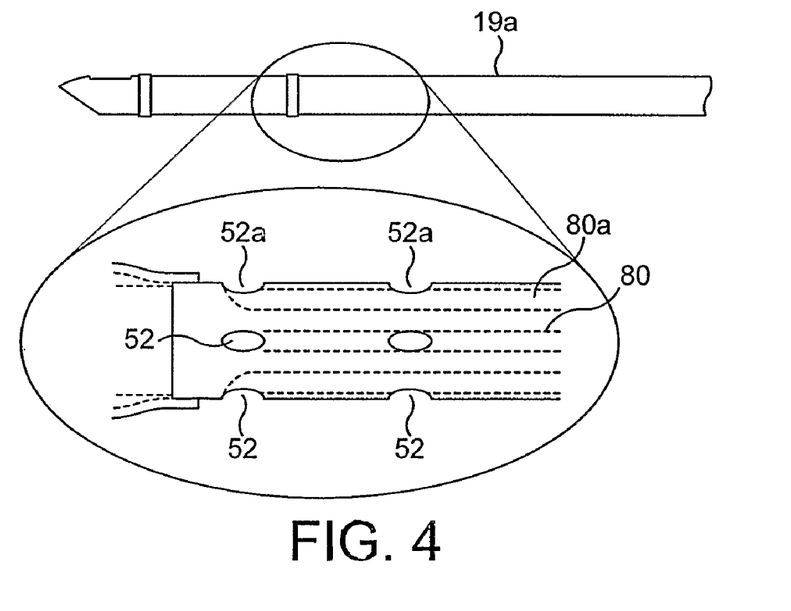
FIG. 4 is a magnified view of a further embodiment of ETT according to the invention.

Referring particularly to FIGS. 3 and 4, it can be seen that the apparatus 19 includes means 19e to facilitate removal of fluid on the mouth side portion 19d of the apparatus 19 in the form of ports 52. Ports 52 are elliptical apertures formed in the wall of the tube 19a, and are regularly spaced around its circumference in three places in this embodiment. Each port 52 opens into a conduit 80. The conduits 80 are formed integrally in the material of the wall 19a, by techniques well known in the art, and extend from the ports 52, along most of the length of the tube 19a, terminating in an aperture 81 (FIG. 2) which is located to be outside of the patient when the tube 19a is in place. In the embodiment illustrated in FIG. 2, the aperture 81 takes the form of the open end of a drain/suction tube 82, which extends away from the tube 19a at its distal end. The end of drain/suction tube 82 may be suitably modified to enable attachment of a suction device (not shown). In this embodiment, conduits 80 are coated on their inner surfaces with parylene. Parylene is a known substance with anti-friction properties.

Referring in particular to FIG. 4, there is illustrated an alternative embodiment of apparatus 19 according to the invention, which has further ports 52 spaced longitudinally as well as circumferentially on the tube 19a.

Figure 5:
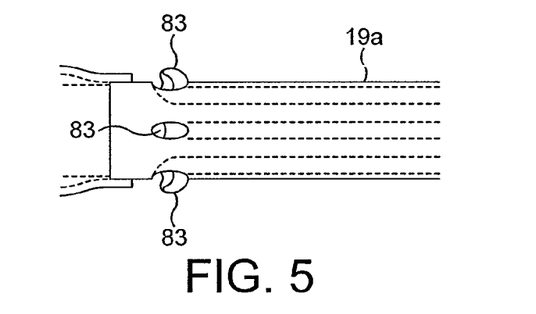
FIG. 5 is a magnified view of a yet further embodiment of ETT according to the invention.
Figure 6:
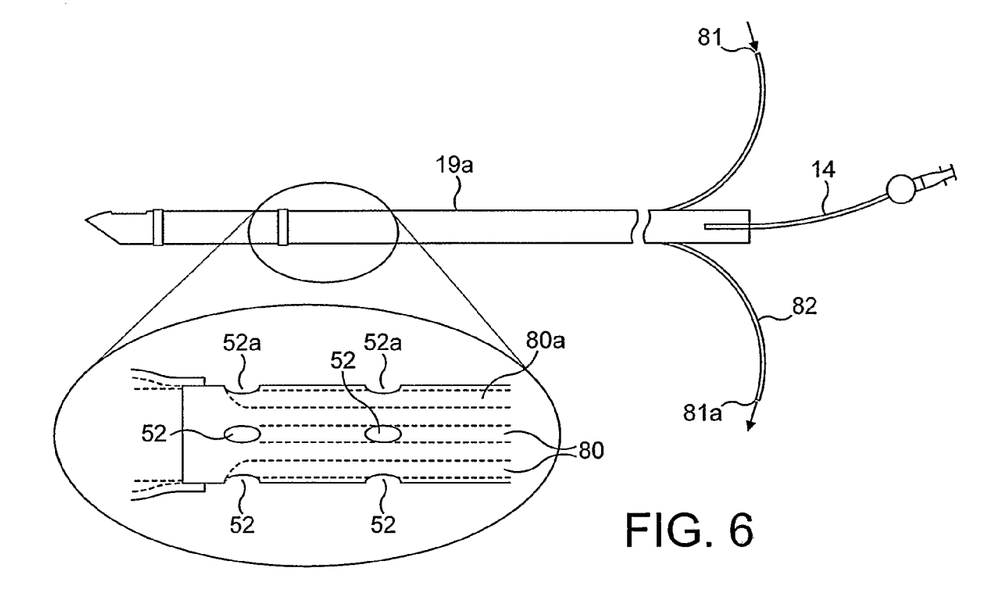
FIG. 6 is a magnified view of a yet further embodiment of ETT according to the invention.
Figure 7A:
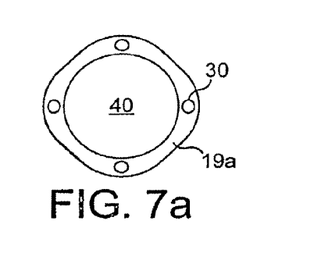
FIGS. 7a, 7b, 7c and 7d show magnified transverse sectional views of the ETT of FIG. 2 taken along the line 4-4.
Figure 7B:
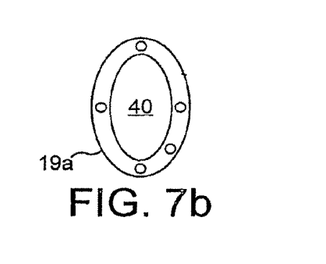
Figure 7C:
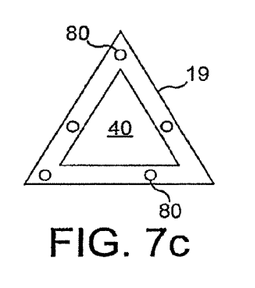
Figure 7D:
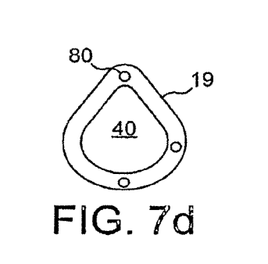

Referring in particular to FIG. 5, there is illustrated a further embodiment of apparatus 19 according to the invention. In this embodiment the ports 52 are provided with protuberances 83 in the form of upstands, or cowls which extend away from the tube 19a wall. The precise form of the protuberances is not particularly important as long as they extend roughly perpendicularly to the major axis of the tube 19a, thereby acting as spacers between the tube 19a and the tracheal wall of a patient, in use.

In FIG. 4, a yet further embodiment of apparatus 19 according to the invention is illustrated. In this embodiment there are two sets of ports first ports 52 and second ports 52a. Ports 52 open into first conduits 80, and ports 52a open into second conduit 80a. Conduit 80 terminates at the distal end of tube 19a in first aperture 81, and conduit 80a terminates in second aperture 81a. There is no interconnection between the first and second sets of ports and conduits, enabling a cleaning or flushing fluid to be inserted via one set, and removed via the other.

FIGS. 7a to 7d illustrate a series of optional cross-sectional profiles for the tube 19a of FIG. 2. Such profiles may include a variety of symmetric and non-symmetric cross section shapes including elliptical and triangular. The cross sectional diameter may also vary along the length of the tube 19a in order that the profile at a particular position within the air passage of a patient is optimised for easy insertion and then optimal fit at a particular position. Additionally, the figure shows that the wall thickness may also be variable at different circumferential and length-wise positions along the tube.

Figure 8A:
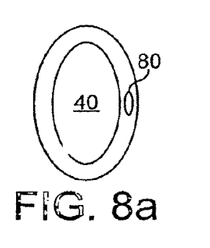
FIGS. 8a, 8b, 8c and 8d are further magnified transverse sectional views of the ETT of FIG. 2 taken along the line 4-4 showing further embodiments.
Figure 8B:
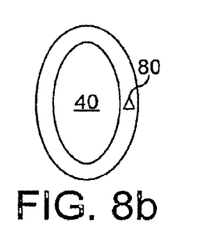
Figure 8C:
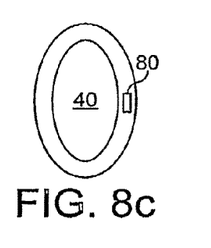
Figure 8D:
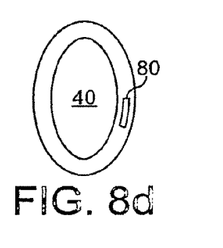

FIGS. 8a to 8d illustrate a series of cross-sectional profiles through the tube 19a showing a variety of possible conduit 80, 80a profiles. Such profiles may include a variety of symmetric and non-symmetric cross section shapes including circular, ovular, oviform, rectangular, elliptical, curved, and triangular. In a particularly advantageous embodiment, the profile may be shaped to mirror or correspond to that of the lumen 40 as shown in FIG. 8d. The precise shape can be chosen to maximise or optimise flow and reduce the chance of blockage whilst minimising the cross sectional thickness of tube 19a. The cross section of the conduits 80, 80a may also vary along the length of the tube in order that the profile at a particular position would further maximise or optimise flow and reduce the chance of blockage.

FIG. 9 shows a magnified view of the region 32 of reduced diameter. As shown, the outer diameter of region 32, OD1, is reduced from the outer diameter of the rest of tube 19a, OD2. As a result of the differing outer diameters, the thickness T1 of the wall of tube 19a in region 32 is less than the thickness T2 of the wall of the remainder of tube 19a. Inflation lumen 30 is defined in the wall of hollow tube 19a in the regions where the wall thickness is T2 (i.e., in regions outside the zone 32 of reduced diameter).

As shown, cuff 20 can be mounted to tube 19a at extreme ends of region 32 at locations 24 and 26 (i.e., locations 24 and 26 are adjacent to the junctions between region 32 and other portions of the tube outside of region 32).

Typically, for an adult size ETT, the distance between the mounting locations 24 and 26 is about three to five centimeters. Also, a relatively short rigid extension tube 36 extends from inside lumen 30, through cuff mounting location 24, and into the interior volume of cuff 20. Accordingly, inflation and deflation of cuff 20 can be controlled by an air supply, such as a syringe or automated pressure control device, coupled to the proximal end of inflation lumen 30 (near the proximal end of hollow tube 19a).

Since hollow tube 19a is made from silicone, the thickness of the tube wall T2 is greater than would be required if the tube were made of a more rigid material such as PVC. Accordingly, for a given inner diameter, ID, the outer diameter OD2 of tube 19a is greater than the outer diameter that would be required if tube 19a were made of PVC. The larger outer diameter OD2 of tube 19a increases the difficulty of insuring that a cuff attached to tube 19a will reach its pressure plateau prior to making circumferential contact with the inner lining of the trachea. However, to compensate for the increased tube outer diameter, which is a consequence of using silicone to fabricate tube 19a, the tube 19a is provided with region 32 of reduced diameter. Attaching cuff 20 to the region 32 of reduced diameter increases the amount by which the cuff expands before it makes circumferential contact with the inner lining of the trachea and thereby facilitates insuring that cuff 20 reaches its pressure plateau prior to making such circumferential contact.

In one example embodiment of an adult size ETT, the inner diameter ID of tube 19a is about seven millimeters, the wall thickness T2 is about 1.625 millimeters, the wall thickness T1 in region 32 is about 1.0 millimeters, the outer diameter ODI of the tube 19a in region 32 is between 1 and 20 millimeters, and the outer diameter OD2 of the majority of tube 19a is about 1 and 20 millimeters. The pressure plateau of cuff 20 is about thirty to thirty five centimeters of water and is reached when the cuff diameter is less than the smallest expected adult tracheal diameter (e.g. less than about 1.5 centimeters).

In yet another example embodiment of an adult size ETT, the inner diameter ID of tube 19a is about eight millimeters, the wall thickness T2 is about 1.625 millimeters, the wall thickness T1 in region 32 is about 1.125 millimeters, the outer diameter ODI of the tube 19a in region 32 is about 10.25 millimeters, and the outer diameter OD2 of the majority of tube 19a is about 11.25 millimeters. Again, the pressure plateau of cuff 20 is about thirty to thirty five centimeters of water and is reached when the cuff diameter is less than the smallest expected adult tracheal diameter (e.g., less than about 1.5 centimeters).

As noted above, inflation lumen 30 is defined in the wall of hollow tube 19a in the regions where the wall thickness is T2 (i.e. in regions outside the region 32 of reduced diameter). The presence of inflation lumen 30 in the wall of hollow tube 19a is one aspect of the ETT 19 that limits the tube's minimum wall thickness. Advantageously, the lumen 30 does not extend beyond the region 32 of reduced diameter, e.g. the lumen extends from near the proximal end of the tube 19a to the reduced diameter portion 32. A relatively short rigid hollow tube 36 is inserted within the lumen 30 and extends through the balloon mounting location 24 to provide fluid communication between lumen 30 and the interior of cuff 20.

If the wall thickness T1 of the region 32 of reduced diameter is too thin, the intra-cuff pressure of cuff 20 (which is circumferentially applied to the outer wall of region 32, and in effect squeezes region 32 inwards), may be sufficient to cause the region 32 of reduced diameter to collapse. Such collapse of any portion of hollow tube 19a is of course not desired since it may occlude the airway lumen 40 provided by the ETT thereby preventing adequate ventilation of the lungs. One method of preventing such collapse is to fabricate the cuff 20 from silicone having a durometer of about 10 Shore A.

Use of a silicone cuff with such a hardness allows the pressure plateau to occur as low as thirty to thirty five centimeters of water, a pressure which will not harm the tracheal mucosa or allow the tube to collapse under normal operating conditions.

Referring again to FIG. 9 it can be seen that tube 19a may be fabricated such that inflation lumen 30 initially extends from the proximal end of tube 19a to a location 30d near the distal end of tube 19a. Using a lathe or other device for cutting material away from a portion of tube 19a so as to form region 32 of reduced diameter automatically connects inflation lumen 30 to the region 32, at location 30e, as long as enough material is removed from the outer portion of the tube to expose lumen 30. Rigid tube 36 may be used thereafter to couple inflation lumen 30 to the interior volume of cuff 20 as discussed above.

Figure 10:
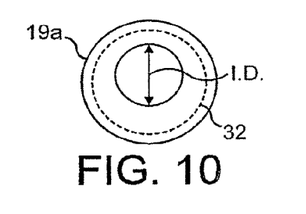
FIG. 10 shows a transverse sectional view of one embodiment of an ETT constructed according to the invention, the view being taken in the general direction of line 4-4 as shown in FIG. 2.
Figure 11:
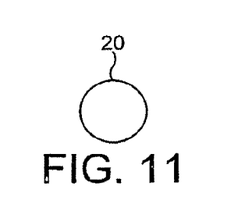
FIG. 11 shows a transverse sectional view of a tube of elastic material used to form a cuff for the tube shown in FIG. 7, the elastic material being circumferentially stretched while forming the cuff.

FIG. 10 shows a transverse sectional view of tube 19a of an ETT constructed according to the invention, the view being taken in the general direction of line 4-4 as shown in FIG. 2. In FIG. 10, the circle labeled 19a represents the outer periphery of the majority of tube 19a (the outer diameter of which is OD2); the dashed circle labeled 32 represents the outer periphery of the region 32 of reduced diameter of tube 19a (the outer diameter of which is OD1); and the circle interior to 32, the diameter of which is labeled, represents the interior lumen 40, or airway passage, which extends from the proximal end to the distal end of tube 19a. In FIG. 11, the circle labeled 20 represents a tube of elastic material, seen in a cross section taken in the same general direction as the cross section of FIG. 10, that will be used to form cuff 20. For convenience of illustration, the inflation lumen 30 is not shown in FIG. 11. As shown, when the cuff material is in its natural resting (unstretched) state, its diameter is less than that of region 32.

So, placing the cuff material over tube 19a and locating it in region 32 advantageously results in circumferentially pre-stretching the cuff material. It will be appreciated that the cuff material may also be pre-stretched both circumferentially and longitudinally.

FIG. 10 shows the airway passage (the diameter of which is ID) as being concentrically located within tube 19a. However, it may be advantageous to form the airway passage so that it is eccentrically located within tube 19a.

Figure 12:
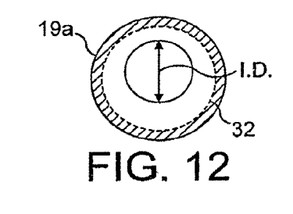
FIG. 12 shows an alternative embodiment of ETT constructed according to the invention having an eccentric airway lumen.

FIG. 12 shows an example of such an eccentrically located airway lumen 40. The eccentricity enables the tube 19a to bend more easily along the portion of the tube with the increased thickness. The eccentricity can help reduce the pressure applied to the trachea when the ETT 19 is in place. As with FIG. 11, for convenience of illustration, the inflation lumen 30 is not shown in FIG. 12.

As discussed above, tube 19a is preferably fabricated from silicone. However, other materials may be used as well. In particular, it may be advantageous to form tube 19a from a material that is harder than silicone such as PVC. Use of a harder material such as PVC allows the outer diameter ODI of the tube 19a outside the region 32 to be reduced as compared with that of a silicone tube. In one embodiment, a region 32 of reduced diameter is formed in a PVC tube 19a by reducing the external diameter by 10% over the length of the tube onto which the cuff is mounted.

As discussed above, adhering a silicone cuff 20 to a PVC tube 19a is more difficult than adhering a silicone cuff to a silicone tube. However, shrink wrap material may be used to attach a silicone cuff 20 to a PVC tube 19a. The shrink wrap material may be configured for example as a tube or annular ring, which is shrunk over the two materials so as to hold the cuff 20 to the tube 19a. When shrink wrap material is used to hold cuff 20 to tube 19a, the cuff 20 may tend to roll or slide in a longitudinal direction when the cuff is inflated. For example, referring to FIG. 6, at location 24 the cuff 20 may tend to roll or slide to the left (towards the proximal end of the ETT 19) upon inflation. One advantage of placing locations 24, 26 within the region 32 of reduced diameter, is that any such rolling or sliding will cause the shrink wrap material to abut into the thicker part of the tube 19a (i.e., where the wall thickness is T2) and this abutment tends to hold the shrink wrap material in place. Additionally, since shrink wrap material adds thickness, it can be used to minimize or eliminate a "step" or rough spot, at the junction of region 32 with the rest of tube 19a. Accordingly, it can be advantageous for locations 24, 26 to be at the extreme ends of region 32 so that the locations 24, 26 abut the thicker part of the tube 19a. However, as shown in FIG. 9 it can also be advantageous for locations 24, 26 to be outside of region 32. Alternatively, it is also possible to have one of locations 24, 26 be within region 32 and have the other one be outside of region 32.

In addition, or as an alternative, to the use of shrink wrap material, other methods, such as laser welding, heat welding, ultrasonic welding, or use of adhesives, may be employed for attaching cuff 20 to hollow tube 19a. However, use of shrink wrap material is preferred for adhering a silicone cuff to a PVC tube, whereas other methods such as welding are preferred for adhering a silicone cuff to a silicone tube.

In use, apparatus 19a is inserted into a patient in exactly the same manner as prior art devices. The apparatus 19a is operated in a similar way to provide an artificial airway in a patient, with the cuff 20 providing a seal between the tracheal wall of the patient and the apparatus 19 to prevent escape of gases which should be passing to the patient's lungs. Over time, liquids, such as the patient's own secretions gather and pool on the mouth side portion 19d of the apparatus 19. These liquids are removed by applying suction to an aperture 81, the liquids being drawn into the ports 52, passing down the conduit 80 and out of the aperture 81 itself. Where it is known in advance that apparatus 19 will need to be inplace in a patient for a particularly extended period, apparatus 19 including two sets of port/conduit/aperture combinations can be installed (FIG. 6) thus enabling a flushing liquid, such as saline with an antibiotic, to be passed into the trachea to break up more viscous accumulations, inhibit bacterial growth, and entrain any such material for removal by suction.

The invention claimed is:

1. Apparatus for use in establishing an artificial airway in a patient, the apparatus comprising:
    a tube for introduction into the patient's trachea for passage of gases to and from the patient's lungs;
    an inflatable seal disposed on the tube to provide, when inflated, a seal between the tube and the trachea of the patient when the device is in use, the seal thereby defining a lung-side portion of the apparatus and a mouth-side portion of the apparatus; and
    a plurality of ports integrally formed in a wall of the tube on the mouth-side portion to facilitate removal of fluid from the mouth-side portion of the apparatus, the ports being circumferentially spaced around the tube, each port opening into a conduit,
    wherein each conduit is formed integrally in the wall of the tube, each conduit being in fluid communication with a single aperture located outside of the patient when the apparatus is in use such that suction applied to the single aperture causes fluid to pass into each port, along each conduit and out of the aperture.

2. Apparatus according to claim 1, wherein the ports are longitudinally spaced on the tube.

3. Apparatus according claim 2, each conduit including on its inner surface a material adapted to reduce friction, reduce adhesion of material passing through the conduit, and reduce or inhibit microbiological growth.

4. Apparatus according to claim 3, wherein said material is selected from the set consisting of parylene and hydrogel-derived materials.

5. Apparatus according to claim 2, further comprising a valve disposed to limit fluid flow direction in each conduit.

6. Apparatus according to claim 2, wherein each port further comprises at least one protrusion or upstand to prevent blockage by ingress of tissue.

7. Apparatus according to claim 6, wherein the at least one protrusion or upstand extends from the wall of the tube adjacent to each port.

8. Apparatus according to claim 1, the tube defining a first zone and a second zone, at least a portion of the first zone having a first outer diameter, the second zone having a second outer diameter, the first outer diameter being smaller than the second outer diameter, the first zone being adjacent to the second zone and the first and second zones being configured for insertion into the patient's trachea, the inflatable seal comprising a cuff attached to the tube such as to extend over at least a portion of the first zone.

9. Apparatus according to claim 8, wherein the cuff is characterized by an unstretched diameter smaller than the first outer diameter.

10. Apparatus according to claim 8, the cuff and/or the tube comprising silicone.

11. Apparatus according to claim 1, wherein the tube comprises an endotracheal tube.

12. Apparatus according to claim 1, wherein the tube comprises a tracheostomy tube.

13. A method of providing an artificial airway in a patient, the method comprising:
    introducing a tube into an inserted location of the patient's trachea for passage of gases to and from the patient's lungs, an inflatable seal being disposed on an outer surface of the tube;
    inflating the seal to provide a seal between the tube and the trachea of the patient when the tube is at the inserted location, the seal thereby defining a lung-side portion of the tube and a mouth-side portion of the tube; and
    removing fluid from the mouth-side portion of the tube using a plurality of ports integrally formed in a wall of the tube on the mouth-side portion, the ports being circumferentially spaced around the tube, each port opening into a conduit, each conduit being formed integrally in the wall of the tube, each conduit being in fluid communication with a single aperture located to be outside the patient when the tube is in use.

14. A method according to claim 13, wherein the step of removing fluid further comprises applying suction to the aperture of the apparatus to remove fluid from the mouth-side of the apparatus via the ports and conduits.

* * * * *